United States Patent [19]

Tegeler et al.

[11] Patent Number: 4,985,450

[45] Date of Patent: Jan. 15, 1991

[54] ARYLTHIADIAZOLYLSULFONAMIDES AND DERIVATIVES

[76] Inventors: John J. Tegeler, 40 Highland Ave., Bridgewater, N.J. 08807; Kirk D. Shoger, 16A Rutgers Rd., Piscataway, N.J. 08854

[21] Appl. No.: 393,494

[22] Filed: Aug. 14, 1989

Related U.S. Application Data

[62] Division of Ser. No. 189,919, May 3, 1988, Pat. No. 4,873,239, which is a division of Ser. No. 8,225, Jan. 29, 1987, Pat. No. 4,758,578.

[51] Int. Cl.$^5$ .................. C07D 285/08; A61K 31/41
[52] U.S. Cl. ............................. 514/361; 514/236.2; 514/227.8; 514/255; 514/326; 546/209; 544/60; 544/134; 544/367; 548/129
[58] Field of Search .................. 548/129; 546/209; 544/134, 60, 367; 514/361, 236.2, 227.8, 255, 326

[56] References Cited

U.S. PATENT DOCUMENTS 3,859,296  1/1975  Phillips .................. 548/129

*Primary Examiner*—Robert Gerstl

[57] ABSTRACT

There are described compounds of the formula

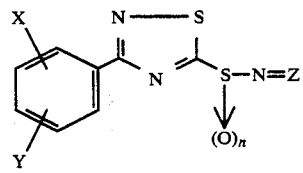

where n is 0, 1 or 2; x and y are independently hydrogen, loweralkyl, loweralkoxy, arylloweralkyl, aryloxy, halogen, $-CF_3$, $-NO_2$, $-OH$, $-OCOR_1$,

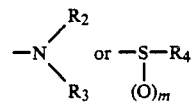

where $R_1$ is loweralkyl, arylloweralkyl, aryl or loweralkoxy, $R_2$ is hydrogen, loweralkyl or loweralkylcarbonyl, $R_3$ is hydrogen or loweralkyl, or the group $-NR_2R_3$ whole is

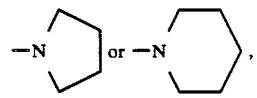

m is 0, 1 or 2, and $R_4$ is hydrogen, loweralkyl or aryl; and Z is ($R_5$, $R_6$),

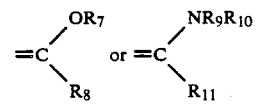

where $R_5$ and $R_6$ are each independently hydrogen or loweralkyl, $R_7$ loweralkyl, $R_8$ is hydrogen, loweralkyl or aryl, $R_9$ and $R_{10}$ are each independently loweralkyl or the group $-NR_9R_{10}$ as a whole is

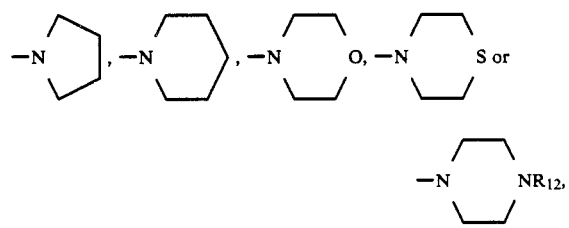

$R_{12}$ being hydrogen, loweralkyl or aryl, and $R_{11}$ is hydrogen, loweralkyl or aryl; which are useful for the treatment of glaucoma.

60 Claims, No Drawings

ARYLTHIADIAZOLYLSULFONAMIDES AND DERIVATIVES

This is a division of prior application, Ser. No. 189,919, filed May 3, 1988, now U.S. Pat. No. 4,873,239, which is a division of prior application Ser. No. 008,225, filed Jan. 29, 1987, now U.S. Pat. No. 4,758,578.

This invention relates to compounds of the formula,

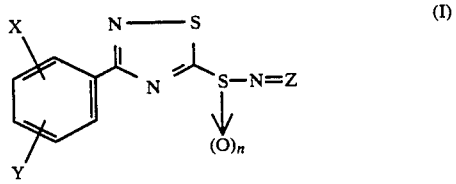

(I)

where n is 0, 1 or 2; X and Y are independently hydrogen, loweralkyl, loweralkoxy, arylloweralkyl, aryloxy, halogen, —CF$_3$, —NO$_2$, —OH, —OCOR$_1$,

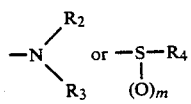

where R$_1$ is loweralkyl, arylloweralkyl, aryl or loweralkoxy, R$_2$ is hydrogen, loweralkyl or loweralkylcarbonyl, R$_3$ is hydrogen or loweralkyl, or the group —NR$_2$R$_3$ as a whole is

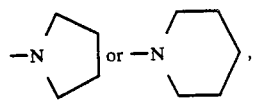

m is 0, 1 or 2, and R$_4$ is hydrogen, loweralkyl or aryl; and Z is (R$_5$, R$_6$),

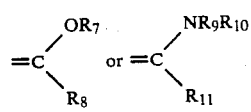

where R$_5$ and R$_6$ are each indenpendently hydrogen or loweralkyl, R$_7$ is loweralkyl, R$_8$ is hydrogen, loweralkyl or aryl, R$_9$ and R$_{10}$ are each independently loweralkyl or the group —NR$_9$R$_{10}$ as a whole is

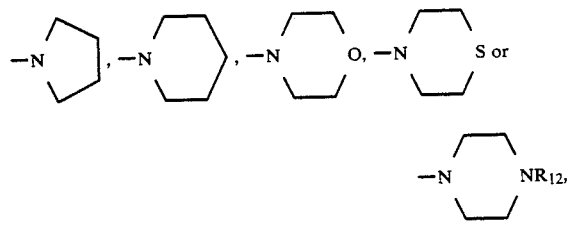

R$_{12}$ being hydrogen, loweralkyl or aryl, and R$_{11}$ is hydrogen, loweralkyl or aryl; which are useful for the treatment of glaucoma; a pharmaceutical composition comprising an effective glaucoma alleviating amount of such a compound and a method of treating a patient in need of relief from glaucoma by use of such a compound.

Throughout the specification and the appended claims, a given chemical formula or name shall encompass all stereo, optical, and geometrical isomers thereof where such isomers exist, as well as pharmaceutically acceptable salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen, —CF$_3$ or —NO$_2$.

The compounds of formula I of this invention are prepared by following one or more of the reaction steps described below. Throughout the description of the synthetic steps, the definitions of n, X, Y, Z, m, R$_1$ through R$_{12}$ are as given above unless otherwise stated or indicated, and the other nomenclatures appearing below shall have the respective meanings as defined in their first appearances unless otherwise stated or indicated.

STEP A

A compound of formula II where X' and Y' are each independently hydrogen, loweralkyl, loweralkoxy, arylloweralkyl, aryloxy, —CF$_3$, —NO$_2$, —NR$_2$R$_3$ or

or halogen is reacted with hydroxylamine in a manner known to the art to afford a compound of formula III.

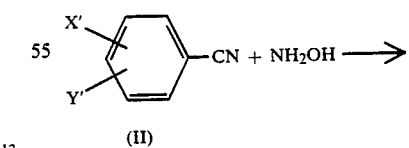

(II)

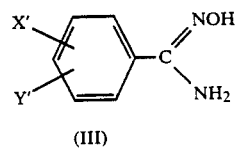

(III)

This type of reaction is disclosed, for instance, in Stephenson, et al. J. Chem. Soc. (C), 861-864 (1969).

STEP B

Compound III is reacted with carbon disulfide in a manner known to the art to afford a compound of formula IV.

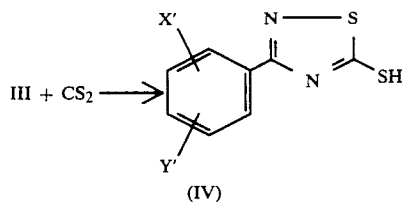

This type of reaction is disclosed, for instance, in Crayen, Chem. Ber. 24, 385-393 (1891).

STEP C

Compound IV is reacted with sodium hypochlorite, calcium hypochlorite or chlorine to convert the —SH group to —SCl group and the resultant product (usually without isolation) is reacted with ammonia (ammonium hydroxide) or amine of the general formula $NHR_5R_6$ to afford a compound of formula V.

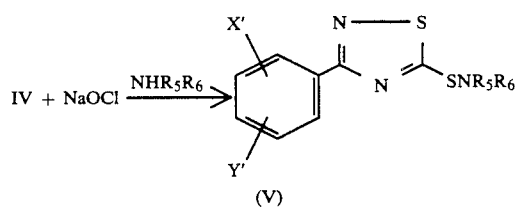

The above reaction is typically conducted in an aqueous medium containing a base such as sodium or potassium hydroxide and by stirring the reaction mixture at a temperature between about $-5°$ and $+35°$ C.

STEP D

Compound V is oxidized with m-chloroperoxybenzoic acid (MCPBA) to afford a sulfinamide compound of formula VI.

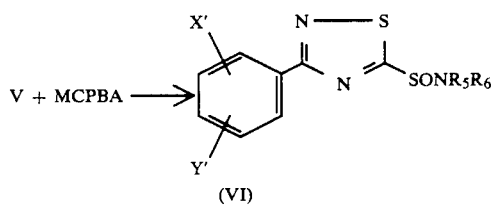

The above oxidation is typically conducted by choosing the molar ratio between MCPBA and compound V at a value slightly in excess of 1, using a suitable solvent including ethereal solvents, halogenated hydrocarbons and polar aprotic solvents and stirring the reaction mixture at a temperature between about $-70°$ and $+30°$ C.

STEP E

Compound V is oxidized with a peracid such as peroxyacetic acid, m-chloroperoxybenzoic acid, hydrogen peroxide or potassium permanganate acid to afford a sulfonamide compound of formula VII.

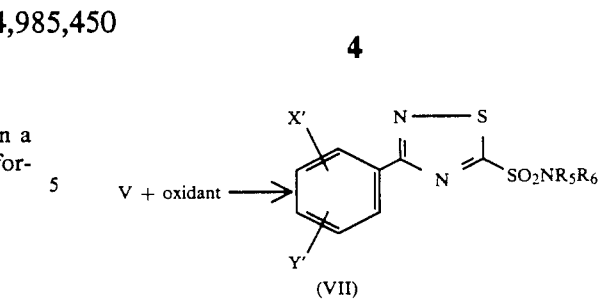

The above oxidation is typically conducted by choosing the molar ratio between an oxidant and compound V at a value slightly in excess of 2, using a suitable solvent including ethereal solvents, halogenated hydrocarbons, water and polar aprotic solvents and stirring the reaction mixture at a temperature between about $0°$ and $100°$ C.

STEP F

A compound of formula VIII obtained from STEP C, D or E is reacted with pyridine hydrochloride to afford a compound of formula IX.

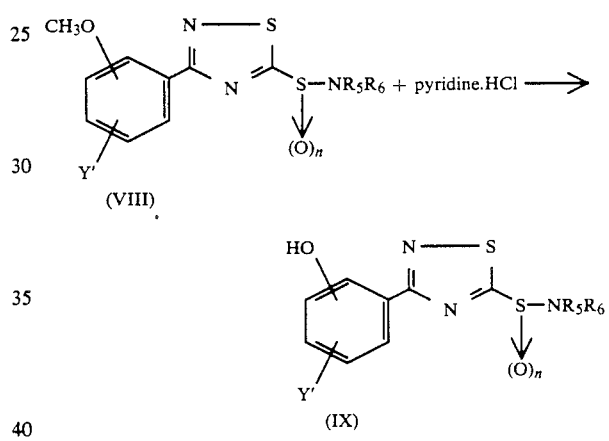

The above reaction is typically conducted by heating a mixture of the two reactants at a temperature of about $150°-210°$ C.

Where the group Y' in formula VIII is methoxy, one can cleave either one of the two methoxy groups according to the above reaction formula or both of them by making a suitable selection of reaction conditions as known in the art.

STEP G

A compound of formula X where the groups X" and Y" are each independently hydrogen, loweralkyl, loweralkoxy, arylloweralkyl, aryloxy, halogen, —CF$_3$, —NO$_2$, —NR$_2$R$_3$,

or —OH obtained from STEP C, D, E or F is reacted with an ortho-ester of the formula

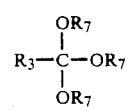

where the groups $R_7$ and $R_8$ are as defined earlier to afford a compound of formula XI.

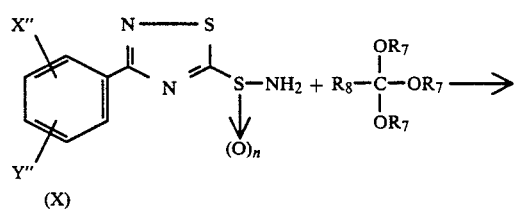

(X)

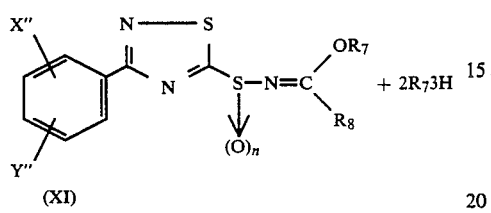

(XI)

The above reaction is typically conducted by heating a mixture of the two reactants optionally in the presence of a suitable solvent such as ethereal solvent or halogenated hydrocarbon at a temperature of about 25°–100°C.

STEP H

A compound of formula XII obtained from STEP G is reacted with an anhydride compound of the formula $R_1CO-O-COR_1$ or a chloride compound of the formula $R_1COCl$ to afford a compound of formula XIII.

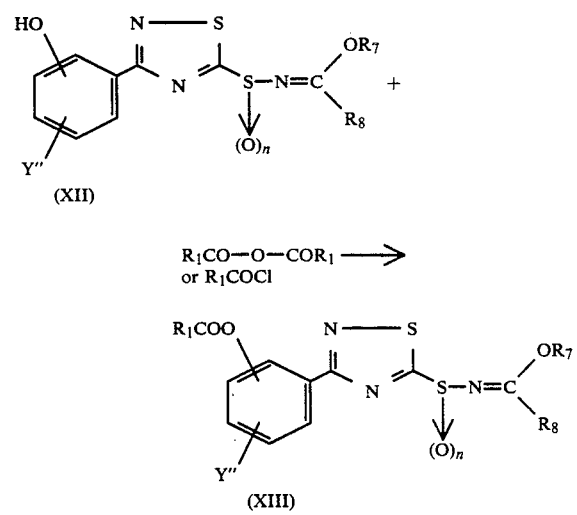

The above reaction is typically conducted by preparing a mixture comprising the two reactants, a suitable tertiary amine such as triethylamine, a suitable solvent such as anhydrous ethereal solvent or polar aprotic solvent and a small amount of 4-dimethylaminopyridine which catalyzes the esterification and stirring the mixture at a temperature between about −10° C. and +50°C.

Where the group Y''' in formula XII is hydroxy, one can esterify only one of the two hydroxy groups according to the above reaction formula or both of them by making a suitable selection of reaction conditions known to the art.

STEP I

A compound of formula XIV where Y is as defined earlier (namely Y may be $R_1COO$) which is obtained from STEP H is hydrolyzed to afford a compound of formula XV.

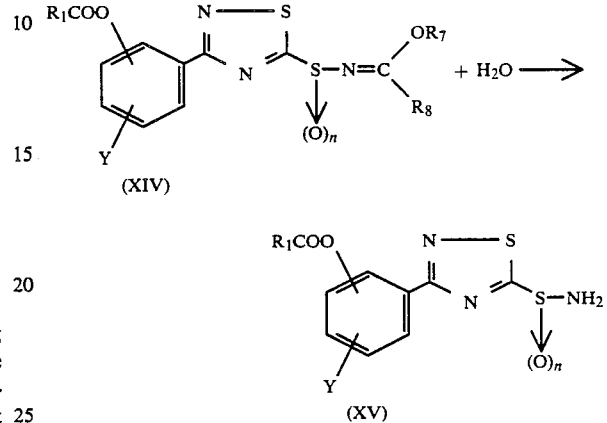

The above hydrolysis is typically conducted by mixing a solution of compound XIV in a suitable water-miscible solvent such as 1,2-dimethoxyethane, methanol, ethanol, or acetone and an aqueous $NaHCO_3$ solution and stirring the resultant mixture at a temperature of about 30°–80°C.

STEP J

A compound of formula XVI obtained from STEP C, D, E, F or I is reacted with thionyl chloride and a compound of the formula $HCONR_9R_{10}$ to afford a compound of formula XVII.

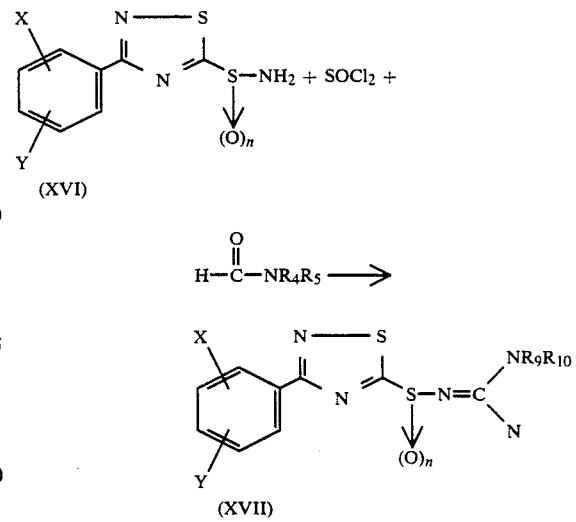

The above reaction is typically conducted by preparing an anhydrous mixture of the reactants optionally with a suitable solvent such as ethereal solvent or halogenated hydrocarbon and thereafter stirring the mixture at a temperature between about −10° C. and +40° C.

STEP K

As an alternative to STEP J, compound XVI is reacted with a compound of formula XVIII to afford a compound of formula XIX.

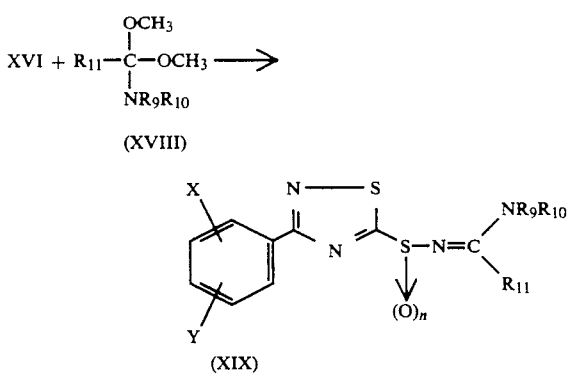

The above reaction is typically conducted in a suitable medium such as anhydrous polar aprotic solvent and stirring the reaction mixture at 25°–60° C.

Compounds of this invention are useful for alleviating glaucoma. The utility of the compounds of this invention for alleviating glaucoma has been evaluated by measuring the ability of test compounds to inhibit carbonic anhydrase esterase and the ability to reduce intraocular pressure. Methods used in this invention for evaluating these abilities are described below.

CARBONIC ANHYDRASE ESTERASE INHIBITION

It is generally known that carbonic anhydrase inhibitors are useful for the treatment of glaucoma. The carbonic anhydrase inhibitory activities have been evaluated by spectrophotometrically measuring the rate of hydrolysis of 1 mM p-nitrophenyl acetate catalyzed by carbonic anhydrase B according to the procedure described in J. Armstrong et al., J. Biol. Chem., Vol 241, No. 21, pp 5137–5149 (1966).

Values of $IC_{50}$ determined for some of the compounds of this invention are presented in Table 1.

TABLE 1

| Compound | Maximum Intraocular Pressure Drop | Carbonic Anhydase Esterase Inhibition |
|---|---|---|
| 3-(2-Chlorophenyl)-1,2,4-thiadiazole-5-sulfonamide | 24.8% at 0.3% | $IC_{50} = 2.7 \times 10^{-7}$ M |
| N-(1-Methoxy-2-methylpropylidene)-3-(2-chlorophenyl)-1,2,4-thiadiazole-5-sulfonamide (prior art compounds) | 13% at 0.3% 26% at 3% | $IC_{50} = 4.0 \times 10^{-7}$ M |
| Acetazolamide | — | $4.8 \times 10^{-7}$ |
| Methazolamide | — | $1.1 \times 10^{-7}$ |
| Timolol | 27.5% at 0.5% 28.0% at 1.0% | |

ALPHA-CHYMOTRYPSIN-INDUCED OCULAR HYPERTENSION

Purpose

The purpose of this procedure is to develop an animal model which displays symptoms of glaucoma. This is done by the direct injection of the proteolytic enzyme, alpha-chymotrypsin into the posterior chamber of the rabbit eye.

Procedure

Ocular hypertension is elicited in New Zealand White rabbits (2.0–2.5 kg) by the injection of alpha-chymotrypsin into the posterior chamber as described by Sears and Sears (Am. J. Ophthalmol. 77, 378–383, (1974). Briefly, the animals are pretreated with indomethacin (10 mg/kg i.p.) to prevent the otherwise immediate onset of inflammation. One hour later, the rabbits are anesthetized with a 2 ml intramuscular injection of a 50:50 mixture of xylazine (20 mg/kg) and ketamine (100 mg/kg). The eyes are individually proptosed and treated topically with 50 microliters of 0.5% proparacaine. The anterior chamber is cannulated with a 30-gauge needle attached to a reservoir set at a pressure of 25 mmHg. Then, 0.5 ml of alpha-chymotrypsin (350 units) is injected through the pupil near the limbus and into the posterior chamber using an S-curved, 30-gauge needle. During the injection, the tip of the needle is swept across the posterior chamber to distribute the enzyme. Care is taken to avoid injection of any enzyme into the corneal stroma. Both needles can then be carefully removed to prevent any significant loss of aqueous humor.

The eyes are examined biweekly for corneal lacerations and overt inflammatory responses. Rabbits demonstrating severe eye inflammation are subsequently discarded from future studies. The intraocular pressures of the operated rabbits are checked approximately four weeks posttreatment. Those exhibiting clear corneas and pressures greater than 30 mmHg (i.e., approximately 10 mmHg above the value observed in normal untreated rabbit eyes) are used for the studying the effect of drugs on intraocular pressure in ocular hypertensive eyes. Generally, about 50% of the operated eyes are suitable for study. Intraocular pressure is measured with a standard instrument and the results are expressed in terms of maximum (over measurment time) percentage drop of intraocular pressure. Results of some of the compounds of this invention are presented also in Table 1.

Intraocular pressure reduction is achieved when the compounds of this invention are administered to a subject requiring such treatment as an effective topical dose of 0.01 to 3.0% solution or suspension. A particularly effective amount is about 3 drops of a 1% preparation per day. It is to be understood, however, that for any particular subject, specific dosage regimens should be adjusted according to the individual need and the professional judgment of the person administering or supervising the administration of the aforesaid compound. It is to be further understood that the dosages set forth herein are examplary only and that they do not, to any extent, limit the scope or practice of the invention.

Examples of the compounds of this invention include:
3-phenyl-1,2,4-thiadiazole-5-sulfenamide;
3-(2-methylphenyl)-1,2,4-thiadiazole-5-sulfenamide;
3-(3-methylphenyl)-1,2,4-thiadiazole-5-sulfenamide;
3-(4-methyphenyl)-1,2,4-thiadiazole-5-sulfenamide;
3-(2-methoxyphenyl)-1,2,4-thiadiazole-5-sulfenamide;
3-(3-methoxyphenyl)-1,2,4-thiadiazole-5-sulfenamide;
3-(4-methoxyphenyl)-1,2,4-thiadiazole-5-sulfenamide;
3-(2-chlorophenyl)-1,2,4-thiadiazole-5-sulfenamide;
3-(3-chlorophenyl)-1,2,4-thiadiazole-5-sulfenamide;
3-(4-chlorophenyl)-1,2,4-thiadiazole-5-sulfenamide;

3-(2-methylphenyl)-1,2,4-thiadiazole-5-sulfinamide;
3-(4-methoxyphenyl)-1,2,4-thiadiazole-5-sulfinamide;
3-(2-chlorophenyl)-1,2,4-thiadiazole-5-sulfinamide;
3-phenyl-1,2,4-thiadiazole-5-sulfonamide;
3-(2-methylphenyl)-1,2,4-thiadiazole-5-sulfonamide;
3-(3-methylphenyl)-1,2,4-thiadiazole-5-sulfonamide;
3-(4-methylphenyl)-1,2,4-thiadiazole-5-sulfonamide;
3-(2-methoxyphenyl)-1,2,4-thiadiazole-5-sulfonamide;
3-(3-methoxyphenyl)-1,2,4-thiadiazole-5-sulfonamide;
3-(4-methoxyphenyl)-1,2,4-thiadiazole-5-sulfonamide;
3-(2-chlorophenyl)-1,2,4-thiadiazole-5-sulfonamide;
3-(3-chlorophenyl)-1,2,4-thiadiazole-5-sulfonamide;
3-(4-chlorophenyl)-1,2,4-thiadiazole-5-sulfonamide;
3-(3-hydroxyphenyl)-1,2,4-thiadiazole-5-sulfonamide;
3-(4-hydroxyphenyl)-1,2,4-thiadiazole-5-sulfonamide;
4-(5-sulfamoyl-1,2,4-thiadiazol-3-yl)phenyl-2,2-dimethylpropionate;
N-(1-methoxyethylidene)-3-(4-hydroxyphenyl)-1,2,4-thiadiazole-5-sulfonamide;
4-[5-[N-(1-methoxyethylidenyl)sulfamoyl]-1,2,4-thiadiazol-3-yl]phenyl-2,2-dimethylpropionate;
N-(1-ethoxyethylidene)-3-phenyl-1,2,4-thiadiazole-5-sulfonamide;
N-(1-ethoxyethylidene)-3-(3-methoxyphenyl)-1,2,4-thiadiazole-5-sulfonamide;
N-(1-ethoxyethylidene)-3-(4-methoxyphenyl)-1,2,4-thiadiazole-5-sulfonamide;
N-(1-methoxybutylidene)-3-(4-methoxyphenyl)-1,2,4-thiadiazole-5-sulfonamide;
M-(1-ethoxyethylidene)-3-(2-chlorophenyl)-1,2,4-thiadiazole-5-sulfonamide;
N-(1-ethoxypropylidene)-3-phenyl-1,2,4-thiadiazole-5-sulfonamide;
N-(1-methoxy-2-methylpropylidene)-3-phenyl-1,2,4-thiadiazole-5-sulfonamide;
N-(1-methoxy-2-methylpropylidene)-3-(2-methylphenyl)-1,2,4-thiadiazole-5-sulfonamide;
N-(1-methoxy-2-methylpropylidene)-3-(2-chlorophenyl)-1,2,4-thiadiazole-5-sulfonamide;
N-(N',N'-dimethylaminomethylene)-3-(2-methylphenyl)-1,2,4-thiadiazole-5-sulfenamide;
N-(N',N'-dimethylaminomethylene)-3-phenyl-1,2,4-thiadiazole-5-sulfonamide;
N-(N',N'-dimethylaminomethylene)-3-(2-methylphenyl)-1,2,4-thiadiazole-5-sulfonamide;
N-(N',N'-dimethylaminomethylene)-3-(2-methoxyphenyl)-1,2,4-thiadiazole-5-sulfonamide;
N-(N',N'-dimethylaminomethylene)-3-(3-methoxyphenyl)-1,2,4-thiadiazole-5-sulfonamide;
N-(N',N'-dimethylaminomethylene)-3-(4-methoxyphenyl)-1,2,4-thiadiazole-5-sulfonamide;
N-(N',N'-dimethylaminomethylene)-3-(2-chlorophenyl)-1,2,4-thiadiazole-5-sulfonamide;
N-(N',N'-dimethylaminomethylene)-3-(4-chlorophenyl)-1,2,4-thiadiazole-5-sulfonamide;
N-(N',N'-diethylaminomethylene)-3-phenyl-1,2,4-thiadiazole-5-sulfonamide;
N-[1-(N',N'-dimethylamino)ethylidene]-3-phenyl-1,2,4-thiadiazole-5-sulfonamide;
N-[1-(N',N'-dimethylamino)ethylidene]-3-(2-methylphenyl)-1,2,4-thiadiazole-5-sulfonamide;
N-(4-morpholinylmethylene)-3-phenyl-1,2,4-thiadiazole-5-sulfonamide;
N-(4-morpholinylmethylene)-3-(2methylphenyl)-1,2,4-thiadiazole-5-sulfonamide;
3-(2-bromophenyl)-1,2,4-thiadiazole-5-sulfenamide;
3-(4-bromophenyl)-1,2,4-thiadiazole-5-sulfenamide;
3-(2-fluorophenyl)-1,2,4-thiadiazole-5-sulfenamide;
3-(4-nitrophenyl)-1,2,4-thiadiazole-5-sulfenamide;
3-(2-isopropylphenyl)-1,2,4-thiadiazole-5-sulfenamide;
3-(4-isopropylphenyl)-1,2,4-thiadiazole-5-sulfenamide;
3-[2-(methylthio)phenyl]-1,2,4-thiadiazole-5-sulfenamide;
3-[2-(trifluoromethyl)phenyl]-1,2,4-thiadiazole-5-sulfenamide;
3-[4-(trifluoromethyl)phenyl]-1,2,4-thiadiazole-5-sulfenamide;
3-(2-bromophenyl)-1,2,4-thiadiazole-5-sulfonamide;
3-(4-bromophenyl)-1,2,4-thiadiazole-5-sulfonamide;
3-(4-ethoxyphenyl)-1,2,4-thiadiazole-5-sulfonamide;
3-(2-fluorophenyl)-1,2,4-thiadiazole-5-sulfonamide;
3-(4-nitrophenyl)-1,2,4-thiadiazole-5-sulfonamide;
3-(4-aminophenyl)-1,2,4-thiadiazole-5-sulfonamide;
3-[2-(methylsulfonyl)phenyl]-1,2,4-thiadiazole-5-sulfonamide;
3-(2-isopropylphenyl)-1,2,4-thiadiazole-5-sulfonamide;
3-(4-isopropylphenyl)-1,2,4-thiadiazole-5-sulfonamide;
3-[2-(trifluoromethyl)phenyl]-1,2,4-thiadiazole-5-sulfonamide;
3-[4-(trifluoromethyl)phenyl]-1,2,4-thiadiazole-5-sulfonamide;
3-[4-(isobutoxycarbonyl)oxyphenyl]-1,2,4-thiadiazole-5-sulfonamide;
N-ethoxymethylene-3-(2-chlorophenyl)-1,2,4-thiadiazole-5-sulfonamide;
N-(1-methoxy-2,2-dimethylpropylidene)-3-(2-chlorophenyl)-1,2,4-thiadiazole-5-sulfonamide;
N-[1-(N',N'-dimethylamino)-2,2-dimethylpropylidene]-1,2,4-thiadiazole-5-sulfonamide;
N-(1-piperidinylmethylene)-3-(4-methoxyphenyl)-1,2,4-thiadiazole-5-sulfonamide;
N-(1-pyrrolidinylmethylene)-3-(4-ethoxyphenyl)-1,2,4-thiadiazole-5-sulfonamide;
N-(4-morpholinylmethylene)-3-(2-methylphenyl)-1,2,4-thiadiazole-5-sulfonamide;
N-(1-methoxy-2,2-dimethylpropylidene)-3-(4-methoxyphenyl)-1,2,4-thiadiazole-5-sulfonamide;
N-[1-(methoxy)phenylmethylene]-3-(4-hydroxyphenyl)-1,2,4-thiadiazole-5-sulfonamide;
3-(4-phenoxyphenyl)-1,2,4-thiadiazole-5-sulfonamide; and
N-methyl-3-(4-ethoxyphenyl)-1,2,4-thiadiazole-5-sulfonamide.

Effective amounts of the compounds of the present invention may be administered to a subject by any one of various methods, for example, orally as in capsules or tablets, parenterally in the form of sterile solutions or suspensions, in some cases intravenously in the form of sterile solutions, or suspensions, and topically in the form of solutions suspensions or ointments, and by aerosol spray. The arylthiadiazolesulfonamides and their derivatives of the present invention, while effective themselves, may be formulated and administered in the form of their pharmaceutically acceptable alkali salts for purposes of increased solubility and the like.

Effective quantities of the compounds of the invention may be administered orally, for example, with an inert diluent or with an adible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.1–30 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral or topical therapeutic administration, the active compounds of the invention may be incorporated into a solution, suspension, ointment or cream. These preparations should contain at least 0.01% of active compound, but may be varied between 0.5 and about 5% of the weight thereof. The amount of active compounds in such compositions is such that a suitable dosage will be obtained. Preferred compositions and preparations according to the present invention are prepared so that a parenteral or topical dosage unit contains between 0.01 to 10 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride of dextrose. The parenteral preparation can be enclosed in ampules or disposable syringes; the topical preparation may be enclosed in multiple dose vials or dropping bottles, made of glass or plastic.

The following examples are presented in order to illustrate this invention.

EXAMPLE 1

3-Phenyl-1,2,4-thiadiazole-5-sulfenamide

A solution of 30 g of 5-mercapto-3-phenyl-1,2,4-thiadiazole in 500 ml of 5% sodium hydroxide and a solution prepared by diluting 310 ml of 5.25% NaOCl to 500 ml with water were added dropwise simultaneously to 1325 ml of an ammonium hydroxide solution while maintaining the mixture at 0° with an ice/methanol bath. The resulting mixture was stirred for 10 minutes and the solids were collected, washed with water and dried under high vacuum (with $P_2O_5$) to give 18.5 g of powder. Recrystallization of 8.2 g of this material from benzene (300 ml) gave 4.8 g of crystals, m.p. >142° dec.

ANALYSIS: Calculated for $C_8H_7N_3S_2$: 45.91%C; 3.37%H; 20.08%N. Found: 45.78%C; 3.28%H; 19.95%N.

EXAMPLE 2

3-(2-Methylphenyl)-1,2,4-thiadiazole-5-sulfenamide

A solution of 56 g of 5-mercapto-3-(2-methylphenyl)-1,2,4-thiadiazole in 870 ml of 5% sodium hydroxide and 130 ml of water and a solution of 280 ml of 10% NaOCl diluted to 1000 ml with water were added dropwise to 2260 ml of an ammonium hydroxide solution while the mixture was stirred and maintained at 0° with an ice/methanol bath. The resulting mixture was stirred for 10 more minutes and the solids were collected, washed with water and dried under high vacuum ($P_2O_5$) to give 43 g of solid, m.p. 110°–112° C.

ANALYSIS: Calculated for $C_9H_9N_3S_2$: 48.40%C; 4.06%H; 18.82%N. Found: 48.28%C; 4.01%H; 18.93%N.

EXAMPLE 3

3-(2-Methoxyphenyl)-1,2,4-thiadiazole-5-sulfenamide

A solution of 4.6 g of 5-mercapto-3-(2-methoxyphenyl)-1,2,4-thiadiazole in 70 ml of 5% sodium hydroxide and a solution prepared by diluting 44 ml of 5.25% NaCl to 70 ml with water were added dropwise simultaneously to 190 ml of ammonium hydroxide solution while maintaining the mixture at 0° with an ice/methanol bath. The resulting mixture was stirred for 10 minutes and the solids were collected, washed with water and dried under high vacuum (with $P_2O_5$) to give 3.0 g of solid, m.p. 136°–138° C. dec.

ANALYSIS: Calculated for $C_9H_9N_3OS_2$: 45.17%C; 3.79%H; 17.56%N. Found: 45.13%C; 3.82%h; 17.41%N.

EXAMPLE 4

3-(3-Methoxyphenyl)-1,2,4-thiadiazole-5-sulfenamide

A solution of 2.2 g of 5-mercapto-3-(3-methoxyphenyl)-1,2,4-thiadiazole in 35 ml of 5% sodium hydroxide and a solution prepared by diluting 22 ml of 5.25% NaOCl solution to 35 ml with water were added dropwise simultaneously to 95 ml of ammonium hydroxide solution while maintaining the mixture at 0°. The resulting mixture was stirred for 15 minutes and the precipitated solid was collected, washed with water and dried ($P_2O_5$/high vacuum) to give 1.76 g of solid, m.p. 157°–160° C. dec.

ANALYSIS: Calculated for $C_9H_9N_3OS_2$: 45.17%C; 3.79%H; 17.56%N. Found: 44.62%H; 3.62%H; 17.35%N.

EXAMPLE 5

3-(4-Methoxyphenyl)-1,2,4-thiadiazole-5-sulfenamide

A solution of 25 g of 5-mercapto-3-(4-methoxyphenyl)-1,2,4-thiadiazole in 350 ml of 5% sodium hydroxide and a solution prepared by diluting 220 ml of 5.25% NaOCl to 350 ml with water were added simultaneously to 950 ml of ammonium hydroxide solution while maintaining the mixture at 0°. The resulting mixture was stirred for 15 minutes and the precipitated solid was collected, washed with water and dried ($P_2O_5$/high vacuum) to give 15.6 g of solid, m.p. 136°–139°.

ANALYSIS: Calculated for $C_9H_9N_3OS_2$: 45.17%C; 3.79%H; 17.56%N. Found: 44.85%C; 3.67%H; 17.44%N.

EXAMPLE 6

3-(2-Chlorophenyl)-1,2,4-thiadiazole-5-sulfenamide

A solution of 25 g of 5-mercapto-3-(2-chlorophenyl)-1,2,4-thiadiazole in 500 ml of 4% sodium hydroxide and a solution prepared by diluting 238 ml of 5.25% NaOCl to 500 ml with water were added dropwise simultaneously to 1020 ml of ammonium hydroxide solution while maintaining the mixture at 0° C. with an ice/methanol bath. The resulting mixture was stirred for 15 minutes and the solids were collected, washed with water and dried under high vacuum ($P_2O_5$) to give 15.4 g of solid, m.p. 143°–145°.

ANALYSIS: Calculated for $C_8H_6ClN_3S_2$: 39.42%C; 2.48%H; 17.24%N. Found: 39.49%C; 2.55%H; 17.13%N.

EXAMPLE 7

3-(3-Chlorophenyl)-1,2,4-thiadiazole-5-sulfenamide

A solution of 41 g of 5-mercapto-3-(3-chlorophenyl)-1,2,4-thiadiazole in 602 ml of 5% sodium hydroxide and a solution prepared by diluting 378 ml of 5.25% NaOCl to 602 ml with water were added dropwise simultaneously to 1634 ml of ammonium hydroxide solution while maintaining the mixture at 0° C. with a salt/ice bath. The resulting mixture was stirred for 30 minutes and the solids were collected, washed with water and dried under vacuum (with $P_2O_5$) to give 5.4 g of solid, m.p. >150° dec.

ANALYSIS: Calculated for $C_8H_6ClN_3S_2$: 39.42%C; 2.48%H; 17.24%N. Found: 39.26%C; 2.37%H; 16.99%N.

EXAMPLE 8

3-(4-Chlorophenyl)-1,2,4-thiadiazole-5-sulfenamide

A solution of 11.5 g of 5-mercapto-3-(4-chlorophenyl)-1,2,4-thiadiazole in 200 ml of 5% sodium hydroxide and a solution prepared by diluting 100 ml of 5.25% NaOCl to 200 ml with water were added dropwise simultaneously to 450 ml of ammonium hydroxide solution while maintaining the mixture at 0° with an ice/methanol bath. The resulting mixture was stirred for 10 minutes and the solids were collected, washed with water and dried under high vacuum (with $P_2O_5$) to give 7.0 g of solid. Recrystallization of 3 g of this material from 1:1 cyclohexane/benzene (200 ml) gave 1.6 g of crystals, m.p. >150° dec.

ANALYSIS: Calculated for $C_8H_6ClN_3S_2$: 39.42%C; 2.48%H; 17.24%N. Found: 39.24%C; 2.31%H; 17.13%N.

EXAMPLE 9

3-(2-Methylphenyl)-1,2,4-thiadiazole-5-sulfinamide hemihydrate

A solution of 3.86 g of 85% m-chloroperoxybenzoic acid (MCPBA) in 100 ml of 1,2-dimethoxyethane (DME) was added to a solution of 4 g of 3-(2-methylphenyl)-1,2,4-thiadiazole-5-sulfenamide in 150 ml of DME at −70° C. over an hour. The resulting solution was stirred for 2 hours at −70° and thereafter at room temperature overnight. Concentration gave a solid which was stirred with 100 ml of sodium bicarbonate solution for 2 hours, collected, washed with water and dried. Recrystallization from cyclohexane/toluene (2:1) gave 2.2 g of solid, m.p. 110°–112°.

ANALYSIS: Calculated for $C_9H_9N_3OS_2.0.5H_2O$: 43.53%C; 4.06%H; 16.92%N. Found: 44.12%C; 3.95%H; 17.42%N.

EXAMPLE 10

3-(4-Methoxyphenyl)-1,2,4-thiadiazole-5-sulfinamide

A solution of 23.9 g of 85% m-chloroperoxybenzoic acid in 125 ml of 1,2-dimethoxyethane (DME hereafter) was added dropwise over 1 hour to a solution of 14 g of 3-(4-methoxyphenyl)-1,2,4-thiadiazole-5-sulfenamide in 300 ml of DME at −5° (ice/methanol bath). The resulting solution was stirred at room temperature overnight. Concentration gave a solid mass which was stirred for 2 hours with 300 ml of saturated sodium bicarbonate solution, collected, washed with water and dried to give 14.8 g of crude product. Flash chromatography using a step gradient of 12 to 15% ethyl acetate/dichloromethane gave 1.37 g of solid, m.p. 144°–147°.

ANALYSIS: Calculated for $C_9H_9N_3O_2S_2$: 42.34%C; 3.55%H; 16.46%N. Found: 42.17%C; 3.67%H; 16.14%N.

EXAMPLE 11

3-(2-Chlorophenyl)-1,2,4-thiadiazole-5-sulfinamide

A solution of 3.45 g of 85% m-chloroperoxybenzoic acid in 100 ml of DME was added to a solution of 4 g of 3-(2-chlorophenyl)-1,2,4-thiadiazole-5-sulfenamide in 150 ml of DME at −70° C. over an hour. The resulting solution was stirred for 2 hours at −70° and thereafter warmed to room temperature. Concentration gave a solid which was stirred with 100 ml of sodium bicarbonate solution overnight. The solid was collected and the filtrate was extracted with ethyl acetate/dichloromethane. Concentration gave 0.7 g of solid which was recrystallized in benzene to give 0.52 g of solid, m.p. 130°–131°.

ANALYSIS: Calculated for $C_8H_6ClN_3OS_2$: 36.99%C; 2.33%H; 16.18%N. Found: 37.59%C; 2.40H; 15.86%N.

EXAMPLE 12

3-Phenyl-1,2,4-thiadiazole-5-sulfonamide

A solution of 30.3 g of 85% m-chloroperoxybenzoic acid in 100 ml of DME was added dropwise at −5° (ice/methanol bath) to 10.5 g of 3-phenyl-1,2,4-thiadiazole-5-sulfenamide in 300 ml of DME over 1hour. The resulting solution was stirred at room temperature overnight and concentrated to a solid mass. The mixture was stirred with 150 ml (2 x) of saturated sodium bicarbonate for 1 hour and filtered. The solids were washed with water and dried under high vacuum (with $P_2O_5$) to give 11 g of solid. Recrystallization from 75% methanol/water gave 7.0 g of solid, 3.8 g of which was flash chromatographed using 5:1 toluene/ether as eluent to give 3.3 g of solid m.p. 191°–193 .

ANALYSIS: Calculated for $C_8H_7N_3O_2S_2$: 39.82%C; 2.92%H; 17.42%N. Found: 39.78%C; 2.90%H; 17.31%N.

EXAMPLE 13

3-(2-Methylphenyl)-1,2,4-thiadiazole-5-sulfonamide

A solution of 47.5 g of 85% m-chloroperoxybenzoic acid in 220 ml of DME was added dropwise to a solution of 20 g of 3-(2-methylphenyl)-1,2,4-thiadiazole-5- sulfenamide in 350 ml of DME at −5° (ice/methanol bath). The resulting solution was stirred at room temperature for 16 hours. Concentration gave a solid mass which was stirred for 1 hour with 650 ml of saturated sodium bicarbonate solution, collected, washed with water and dried to give 24.5 g of crude product. Recrystallization from 3:1 methanol/water (400 ml) gave 16.7 g of solid, m.p., 174°–176°.

ANALYSIS: Calculated for $C_9H_9N_3O_2S_2$: 42.34%C; 3.55%H; 16.46%N. Found: 42.64%C; 3.64%H; 16.14%N.

EXAMPLE 14

3-(2-Methoxyphenyl)-1,2,4-thiadiazole-5-sulfonamide

A solution of 25.2 g of 85% m-chloroperoxybenzoic acid in 140 ml of DME was added dropwise to a solution of 14.2 g of 3-(2-methoxyphenyl)-1,2,4-thiadiazole-5-sulfenamide in 450 ml of DME at −5°. The resulting solution was stirred at room temperature overnight. Concentration gave a mass which was stirred for 1.5 hour with 300 ml of saturated sodium bicarbonate solution, collected, washed with water and dried (high vacuum $P_2O_5$) to give 10.2 g of crude product. Recrystallization from ethanol gave 5.8 g of crystals, m.p. 171°–173°.

ANALYSIS: Calculated for $C_9H_9N_3O_3S_2$: 39.84%C; 3.34%H; 15.49%N. Found: 39.98%C; 3.30%H; 15.45%N.

EXAMPLE 15

3-(3-Methoxyphenyl)-1,2,4-thiadiazole-5-sulfonamide

A solution of 36.8 g of 85% m-chloroperoxybenzoic acid in 200 ml of DME was added dropwise to a solution of 20 g of 3-(3-methoxyphenyl)-1,2,4-thiadiazole-5-sulfenamide in 500 ml of DME at −5° C. over an hour. The resulting solution was stirred at room temperature overnight. Concentration gave a solid mass which was stirred for 2 hours with 450 ml of saturated sodium bicarbonate solution, collected, washed with water and dried to give 21.95 g of crude product. Recrystallization from methanol/water (3:1) gave 17.28 g of crystals, m.p. 166°–169°.

ANALYSIS: Calculated for $C_9H_9N_3O_3S_2$: 39.84%C; 3.34%H; 15.49%N. Found: 40.09%C; 3.38%H; 15.35%N.

EXAMPLE 16

3-(4-Methoxyphenyl)-1,2,4-thiadiazole-5-sulfonamide

A solution of 23.9 g of 85% m-chloroperoxybenzoic acid in 125 ml of DME was added dropwise over 1 hour to a solution of 14 g of 3-(4-methoxyphenyl)-1,2,4-thiadiazole-5-sulfenamide in 300 ml of DME at −5° (ice/methanol bath). The resulting solution was stirred at room temperature overnight. Concentration gave a solid mass which was stirred for 2 hours with 300 ml of saturated sodium bicarbonate solution, collected, washed with water and dried ($P_2O_5$/high vacuum) to give 14.8 g of crude product. Flash chromatography using 5:1 toluene/ether gave 2.4 g of solid, m.p. 184°–185°.

ANALYSIS: Calculated for $C_9H_9N_3O_3S_2$: 39.84%C; 3.34%H; 15.49%N. Found: 40.20%C; 3.38%H; 15.15%N.

EXAMPLE 17

3-(2-Chlorophenyl)-1,2,4-thiadiazole-5-sulfonamide

A solution of 18.0 g of 85% m-chloroperoxybenzoic acid in 100 ml of DME was added dropwise to a solution of 10 g of 3-(2-chlorophenyl)-1,2,4-thiadiazole-5-sulfenamide in 300 ml of DME at −5° (ice/methanol bath). The resulting solution was stirred at room temperature for 26 hours. Concentration gave a solid mass which was stirred with 200 ml of saturated sodium bicarbonate solution for 2 hours, filtered, washed with water and dried ($P_2O_5$/high vacuum) to give 9.0 g of solid. Recrystallization from 3:1 methanol/water (130 ml) gave 7.2 g of crystals, m.p. 183°–185°.

ANALYSIS: Calculated for $C_8H_6ClN_3O_2S_2$: 34.84%C; 2.19%H; 15.24%N. Found: 34.71%C; 2.18%H; 14.90%N.

EXAMPLE 18

3-(3-Chlorophenyl)-1,2,4-thiadiazole-5-sulfonamide

A solution of 5.8 g of 85% m-chloroperoxybenzoic acid in 32 ml of DME was added dropwise over 1 hour to a solution of 3.25 g of 3-(3-chlorophenyl)-1,2,4-thiadiazole-5-sulfenamide in 90 ml of DME at −5° (ice/methanol bath). The resulting mixture was stirred overnight at room temperature. Concentration gave a solid mass which was stirred with 100 ml of saturated sodium bicarbonate solution for 2 hours, filtered, washed with water and dried to give 3.2 g of crude product. This was recrystallized from methanol/water (3:1) to give 2.4 of solid, m.p. 182°–184° C.

ANALYSIS: Calculated for $C_8H_6ClN_3O_2S_2$: 34.84%C; 2.19%H; 15.24%N. Found: 35.10%C; 2.15%H; 14.95%N.

EXAMPLE 19

3-(4-Chlorophenyl)-1,2,4-thiadiazole-5-sulfonamide

A solution of 6.7 g of 85% m-chloroperoxybenzoic acid in 35 ml of DME was added dropwise over 1 hour to a solution of 4.0 g of 3-(4-chlorophenyl)-1,2,4-thiadiazole-5-sulfenamide in 100 ml of DME at −5° (ice/methanol bath). The resulting solution was stirred at room temperature overnight. Concentration gave a solid mass which was stirred with 75 ml of saturated sodium bicarbonate solution for 1.5 hours, filtered, washed with water and dried ($P_2O_5$/high vacuum) to give 4.3 g of crude product. Flash chromatography using 5:1 toluene/ether as eluent gave 2.7 g of solid, m.p. 211°–213°.

ANALYSIS: Calculated for $C_8H_6ClN_3O_2S_2$: 34.84%C; 2.19%H; 15.24%N. Found: 34.73%C; 2.17%H; 14.99%N.

EXAMPLE 20

3-(3-Hydroxyphenyl)-1,2,4-thiadiazole-5-sulfonamide

Pyridine hydrochloride (160 g) was preheated to 205° and 8 g of finely ground 3-(3-methoxyphenyl)-1,2,4-thiadiazole-5-sulfonamide was added. Said temperature was maintained for 15 minutes. The mixture was then poured into ice water (1000 ml) and extracted with ethyl acetate (3×500 ml), and the extracts were washed with saturated sodium chloride solution (500 ml) and dried over anhydrous magnesium sulfate. Concentration gave 5.3 g of product. Flash chromatography using 10% ethyl acetate/dichloromethane as an eluent gave 2.3 g of product. This was combined with 0.7 g of product from a previous reaction and recrystallized in hot water to give 2.2 g of solid, m.p. 191°–192°.

ANALYSIS: Calculated for $C_8H_7N_3O_3S_2$: 37.34%C; 2.74%H; 16.33%N. Found: 37.62%C; 2.695 H; 15.96%N.

EXAMPLE 21

3-(4-Hydroxyphenyl)-1,2,4-thiadiazole-5-sulfonamide

To 35 g of pyridine hydrochloride at 200° was added 28 g of 3-(4-methoxyphenyl)-1,2,4-thiadiazole-5-sulfonamide with stirring. The resulting mixture was maintained at 200°–4° for 10 minutes, cooled slightly, poured into excess ice water and extracted with ethyl acetate (3×). The organics were dried over anhydrous magnesium sulfate and concentrated to give 2.0 g of solid. Flash chromatography using 10% ethyl acetate/dichloromethane as eluent gave 1.0 g of solid. This was combined with 0.5 g of the same compound from a previous reaction and recrystallized from water using decolorizing carbon to give 0.95 g of solid, m.p. 219°–221°.

ANALYSIS: Calculated for $C_8H_7N_3O_3S_2$: 37.34%C; 2.74%H; 16.33%N. Found: 37.11%C; 2.80%H; 16.17%N.

EXAMPLE 22

4-(5-Sulfamoyl-1,2,4-thiadiazol-3-yl)phenyl 2,2-dimethylpropionate

A mixture of 3.95 g of 4-[5-[N-(1-methoxyethylidenyl)-sulfamoyl]-1,2,4-thiadiazol-3-yl]phenyl 2,2-dimethylpropionate (see Example 23 for preparation) in DME (110 ml) and aqueous 4% sodium bicarbonate solution (40 ml) was warmed rapidly with stirring to 80° where it became nearly homogeneous. After cooling in an ice bath the resulting mixture was concentrated to remove the DME and thereafter saturated with sodium chloride. This was extracted with ethyl acetate (3×200 ml) and the organics were washed successively with ½ saturated and saturated sodium chloride solutions and dried over anhydrous magnesium sulfate. Concentration gave 3.3 g of solid which was recrystallized from 2:1 benzene/cyclohexane to give 2.5 g of solid which was taken up in 1,2-dichloroethane, concentrated and dried in vacuo to give 2.1 g of solid, m.p. 176°–178°.

ANALYSIS: Calculated for $C_{13}H_{15}N_3O_4S_2$: 45.73%C; 4.43%H; 12.31%N. Found: 45.79%C; 4.28%H; 12.28%N.

EXAMPLE 23

N-(1-Methoxyethylidene)-3-(4-hydroxyphenyl)-1,2,4-thiadiazole-5-sulfonamide

A mixture of 3.0 g of 3-(4-hydroxyphenyl)-1,2,4-thiadiazole-5-sulfonamide and 20 ml of trimethylorthoacetate was stirred at room temperature for 42 hours. Pentane (25 ml) was added and stirring continued overnight. The precipitated solid was triturated with benzene and collected to give 2.4 g of powder, m.p. 190°–192°.

ANALYSIS: Calculated for $C_{11}H_{11}N_3O_4S_2$: 42.16% C; 3.54% H; 13.41% N, Found: 42.06% C; 3.36% H; 13.42% N.

EXAMPLE 24

4-[5-[N-(1-Methoxyethylidenyl)sulfamoyl]-1,2,4-thiadiazol-3-yl]phenyl 2,2-dimethylpropionate A solution of 3.8 g of N-(1-methoxyethylidene)-3-(4-hydroxyphenyl)-1,2,4-thiadiazole-5-sulfonamide in 60 ml of anhydrous acetone was added over 30 minutes to a solution of 4.9 ml of trimethylacetic anhydride and 5 ml of triethylamine in 10 ml of acetone containing 50 mg of 4-dimethylaminopyridine at −5°. After the mixture had warmed to room temperature, it was concentrated, taken up in ethyl acetate, washed with water, saturated sodium bicarbonate solution and brine, and dried over anhydrous magnesium sulfate. Concentration gave a wet solid which was triturated with cyclohexane and collected to give 4.1 g of solid. Flash chromatography using dichloromethane as an eluent gave 3.4 g of solid, m.p. (soft 162°) 171°–173°.

ANALYSIS: Calculated for $C_{16}H_{19}N_3O_5S_2$: 48.35% C; 4.82% H; 10.57% N. Found: 48.08% C; 4.79% H; 10.48% N.

EXAMPLE 25

N-(1-Ethoxyethylidene)-3-phenyl-1,2,4-thiadiazole-5-sulfonamide

A mixture of 3.0 g of 3-phenyl-1,2,4-thiadiazole-5-sulfonamide and 10 ml of triethyl orthoacetate was warmed at reflux for 4 hours. The mixture was cooled to room temperature and diluted with hexane (30 ml) and the precipitated solid was collected, washed with hexane and dried to give 3.25 g of solid, m.p. 120°–122°.

ANALYSIS: Calculated for $C_{12}H_{13}N_3O_3S_2$: 46.29% C; 4.21% H; 13.50% N. Found: 46.08% C; 4.17% H; 13.50% N.

EXAMPLE 26

N-(1-Ethoxyethylidene)-3-(3-methoxyphenyl)-1,2,4-thiadiazole-5-sulfonamide

Triethyl orthoacetate (5 ml) was added to 1.2 g of 3-(3-methoxyphenyl)-1,2,4-thiadiazole-5-sulfenamide and the mixture was heated to reflux for 3 hours. Upon removal of the heat, a solid formed. The solid was collected and washed with hexane to give 1.38 g of crude product. This was combined with 0.4 g of another crude product from a previous reaction and recrystallized from 100 ml of cyclohexane/benzene (3:1) to yield 1.51 g of crystals, m.p. 125°–127° C.

ANALYSIS: Calculated for $C_{13}H_{15}N_3O_4S_2$: 45.73% C; 4.43% H; 12.31% N. Found: 45.91% C; 4.43% H; 12.21% N.

EXAMPLE 27

N-(1-Ethoxyethylidene)-3-(4-methoxyphenyl)-1,2,4-thiadiazole-5-sulfonamide

A mixture of 1.5 g of 3-(4-methoxyphenyl)-1,2,4-thiadiazole-5-sulfonamide and 5 ml of triethyl orthoacetate was refluxed for 4 hours. The mixture was cooled and diluted with hexane (15 ml), and the solids were collected and washed with hexane to give 1.7 g of solid. Recrystallization from 3:1 cyclohexane/benzne (100 ml) gave 1.16 g of needles, m.p. 156°–158°.

ANALYSIS: Calculated for $C_{13}H_{15}N_3O_4S_2$: 45.73% C; 4.43% H; 12.31% N. Found: 45.83% C; 4.33% H; 12.22% N.

EXAMPLE 28

N-(1-Methoxybutylidene)-3-(4-methoxyphenyl)-1,2,4-thiadiazole-5-sulfonamide

A mixture of 1.5 g of 3-(4-methoxyphenyl)-1,2,4-thiadiazole-5-sulfonamide and 4.1 g of trimethyl orthobutyrate was warmed at reflux for 0.5 hour. The mixture was cooled and triturated with hexane (3×) to give 1.84 g of solid. Recrystallization from cyclohexane/benzene (6:1) gave 1.63 g of fluffy solid. This was combined with 0.7 g sample from another identical small scale reaction. This combined material (2.33 g) had m.p. 159°–161°.

ANALYSIS: Calculated for $C_{14}H_{17}N_3O_4S_2$: 47.31% C; 4.82% N; 11.82% N. Found: 47.17% C; 4.78% N; 11.87% N.

EXAMPLE 29

N-(1-Ethoxyethylidene)-3-(2-chlorophenyl)-1,2,4-thiadiazole-5-sulfonamide

A mixture of 3 g of 3-(2-chlorophenyl)-1,2,4-thiadiazole-5-sulfonamide and 11 ml of triethyl orthoacetate was warmed to reflux for 3.5 hours. The mixture was cooled, triturated with hexane (25 ml) and filtered to give 3.13 g of solid, m.p. 70°–72° C.

ANALYSIS: Calculated for $C_{12}H_{12}ClN_3O_3S_2$: 41.67%C; 3.50%H; 12.15%N. Found: 41.73%C; 3.52%H; 12.09%N.

EXAMPLE 30

N-(1-Ethoxypropylidene)-3-phenyl-1,2,4-thiadiazole-5-sulfonamide

A mixture of 3.0 g of 3-phenyl-1,2,4-thiadiazole-5-sulfonamide and 11 ml of triethyl orthopropionate was warmed in an oil bath at 80° for 4 hours. The mixture was cooled to room temperature and diluted with hexane (35 ml) and the precipitated solid was collected, washed with hexane and dried to give 3.3 g of solid, m.p. 98°–100°.

ANALYSIS: Calculated for $C_{13}H_{15}N_3O_3S_2$: 47.98%C; 4.65%H; 12.91%N. Found: 47.76%C; 4.59%H; 12.90%N.

EXAMPLE 31

N-(1-Methoxy-2-methylpropylidene)-3-phenyl-1,2,4-thiadiazole-5-sulfonamide

A mixture of 3 g of 3-phenyl-1,2,4-thiadiazole-5-sulfonamide and and 11 ml of trimethyl orthoisobutyrate was warmed to about 90° using an oil bath. After 2.5 hours, the solution was allowed to cool to room temperature, whereupon a precipitate formed. Hexane (25 ml) was added to complete the precipitation. The solid was collected, washed with hexane and vacuum dried ($P_2O_5$) to give 3.34 g of solid, m.p. 123°–124°.

ANALYSIS: Calculated for $C_{13}H_{15}N_3O_3S_2$: 47.98%C; 4.64%H; 12.91%N. Found: 48.12%C; 4.81%H; 13.29%N.

EXAMPLE 32

N-(1-Methoxy-2-methylpropylidene)-3-(2-methylphenyl)-1,2,4-thiadiazole-5-sulfonamide A mixture of 3 g of 3-(2-methylphenyl)-1,2,4-thiadiazole-5-sulfonamide and 11 ml of trimethyl orthoisobutyrate was heated to reflux and stirred for 2 hours. The mixture was allowed to cool to room temperature, whereupon a precipitate formed. Hexane was added and the mixture was stirred for 15 minutes. The solid was filtered and washed with hexane and dried in vacuum ($P_2O_5$) to give 3.49 g of solid, m.p. 116°–118°.

ANALYSIS: Calculated for $C_{14}H_{17}N_3O_3S_2$: 49.54%C; 5.05%H; 12.38%N. Found: 49.43%C; 5.06%H; 12.05%N.

EXAMPLE 33

N-(1-Methoxy-2-methylpropylidene)-3-(2-chlorophenyl)-1,2,4-thiadiazole-5-sulfonamide A mixture of 2.9 g of 3-(2-chlorophenyl)-1,2,4-thiadiazole-5-sulfonamide in 11 ml of trimethyl orthoisobutyrate was warmed to about 85° with an oil bath. After 2.5 hours the solution was cooled to room temperature, whereupon a precipitate formed. Hexane (25 ml) was added to insure complete precipitation. The solid was filtered, washed with hexane and vacuum dried ($P_2O_5$) to give 3.08 g of solid, m.p. 75°–76°.

ANALYSIS: Calculated for $C_{13}H_{14}ClN_3O_3S_2$: 43.39%C; 3.92%H; 11.68%N. Found: 43.23%C; 3.87%H; 12.17%N.

EXAMPLE 34

N-(N',N'-Dimethylaminomethylene)-3-(2-methylphenyl)-1,2,4-thiadiazole-5-sulfenamide N,N-Dimethylformamide dimethylacetal (2.7 ml) was added dropwise to a suspension of 3.0 g of 3-(2-methylphenyl)-1,2,4-thiadiazole-5-sulfenamide in 25 ml of anhydrous acetonitrile. The resulting mixture was warmed slightly to homogeneity and thereafter stirred at room temperature overnight. The reaction mixture was concentrated, taken up in ether, washed with water (3×) and saturated sodium chloride solution and dried over anhydrous magnesium sulfate. Concentration gave 3.85 g of an oil which was flash chromatographed with 2% ethyl acetate/dichloromethane used as an eluent to give 2.3 g of an oil.

ANALYSIS: Calculated for $C_{12}H_{14}N_4S_2$: 51.77%C; 5.07%H; 20.13%N. Found: 51.57%C; 5.31%H; 20.27%N.

EXAMPLE 35

N-(N',N'-Dimethylaminomethylene)-3-phenyl-1,2,4-thiadiazole-5-sulfonamide

Thionyl chloride (4.66 ml) was added dropwise to a solution of 3.15 g of 3-phenyl-1,2,4-thiadiazole-5-sulfonamide in 10 ml of anhydrous dimethylformamide at −5°. This mixture was stirred at room temperature for 2 hours and then poured into ice water and stirred for 30 minutes. The solids were collected, washed with water and dried (high vacuum, $P_2O_5$) to give 3.7 g of solid, m.p. (soft 150°) 160°–162°.

ANALYSIS: Calculated for $C_{11}H_{12}N_4O_2S_2$: 44.58%C; 4.08%H; 18.91%N. Found: 44.44%C; 3.99%H; 18.87%N.

EXAMPLE 36

N-(N',N'-Dimethylaminomethylene)-3-(2-methylphenyl)-1,2,4-thiadiazole-5-sulfonamide Thionyl chloride (4.2 ml) was added dropwise to 3.0 g of 3-(2-methylphenyl)-1,2,4-thiadiazole-5-sulfonamide in 12 ml of anhydrous dimethylformamide at −5°. This mixture was stirred at room temperature for 2 hours, poured into ice water and stirred for 30 minutes. The solids were collected, washed with water and taken up in dichloromethane. The organics were washed with water (3×), dried over anhydrous magnesium sulfate, and concentrated to give 3.1 g of solid, m.p. 166°–168°.

ANALYSIS: Calculated for $C_{12}H_{14}N_4O_2S_2$: 46.43%C; 4.55%H; 18.05%N. Found: 46.27%C; 4.58%H; 18.00%N.

EXAMPLE 37

N-(N',N'-Dimethylaminomethylene)-3-(2-methoxyphenyl)-1,2,4-thiadiazole-5-sulfonamide Thionyl chloride (2.11 ml) was added dropwise to 1.6 g of 3-(2-methoxyphenyl)-1,2,4-thiadiazol-5-sulfonamide in 7.5 ml of anhydrous dimethylformamide at −5°. The resulting solution was stirred at room temperature for 3 hours, poured into ice water and stirred for 30 minutes. The precipitated solids were collected, washed with water and taken up in dichloromethane. The organics were washed with water (3×), dried over anhydrous magnesium sulfate, and concentrated to give 1.7 g of solid, m.p. 117°–119°.

ANALYSIS: Calculated for $C_{12}H_{14}N_4O_3S_2$: 44.16%C; 4.32%H; 17.17%N. Found: 44.17%C; 4.25%H; 17.06%N.

EXAMPLE 38

N-(N',N'-Dimethylaminomethylene)-3-(3-methoxyphenyl)-1,2,4-thiadiazole-5-sulfonamide Thionyl chloride (2.33 ml) was added dropwise to 1.75 g of 3-(3-methoxyphenyl)-1,2,4-thiadiazole-5-sulfonamide in 25 ml of dry dimethylformamide at −5°C. The resulting mixture was stirred at room temperature for 2 hours, poured into ice water and stirred for 30 minutes. The solids were collected, washed with water and taken up in dichloromethane. The organics were washed with water (3×), dried over anhydrous magnesium sulfate and concentrated to give a solid which was dried (high vacuum/$P_2O_5$) to give 1.91 g of solid, m.p. (soft 140°) 143°–146° C.

ANALYSIS: Calculated for $C_{12}H_{14}N_4O_3S_2$: 44.16%C; 4.32%H; 17.17%N. Found: 43.58%C; 4.25%H; 16.94%N.

EXAMPLE 39

N-(N',N'-Dimethylaminomethylene)-3-(4-methoxyphenyl)-1,2,4-thiadiazole-5-sulfonamide Thionyl chloride (2.33 ml) was added dropwise to 1.75 g of 3-(4-methoxyphenyl)-1,2,4-thiadiazole-5-sulfonamide in 5 ml of anhydrous dimethylformamide at −5°. The resulting mixture was stirred at room temperature for 2 hours, poured into ice water and stirred for 30 minutes. The solids were collected, washed with water and taken up in dichloromethane. The organics were washed with water (3×), dried over anhydrous magnesium sulfate and concentrated to give a solid which was dried (high vacuum/$P_2O_5$) to give 1.3 g of solid, m.p. (soft 180°) 184°–185°.

ANALYSIS: Calculated for $C_{12}H_{14}N_4O_3S_2$: 44.16%C; 4.32%H; 17.17%N. Found: 43.93%C; 4.28%H; 16.89%N.

EXAMPLE 40

N-(N',N'-Dimethylaminomethylene)-3-(2-chlorophenyl)-1,2,4-thiadiazole-5-sulfonamide Thionyl chloride (2.6 ml) was added dropwise to 2.0 g of 3-(2-chlorophenyl)-1,2,4-thiadiazole-5-sulfonamide in 8 ml of anhydrous dimethylformamide at −5°. The resulting mixture was stirred at room temperature for 4 hours, poured into ice water and stirred for 20 minutes. The solids were collected, washed with water, taken up in dichloromethane, washed with water (3×) and dried over anhydrous magnesium sulfate. Concentration gave 1.8 g of solid, m.p. 158°–160°.

ANALYSIS: Calculated for $C_{11}H_{11}ClN_4O_2S_2$: 39.93%C; 3.35%H; 16.94%N. Found: 39.80%C; 3.30%H; 16.90%N.

EXAMPLE 41

N-(N',N'-Dimethylaminomethylene)-3-(4-chlorophenyl)-1,2,4-thiadiazole-5-sulfonamide Thionyl chloride (1.49 ml) was added dropwise to a solution of 1.15 ml of 3-(4-chlorophenyl)-1,2,4-thiadiazole-5-sulfonamide in 5 ml of anhydrous dimethylformamide at −5°. The resulting mixture was stirred at room temperature for 2 hours, poured into ice water and stirred for 30 minutes. The solids were collected, washed with water and dried (high vacuum/$P_2O_5$) to give 1.1 g of solid, m.p. 209°–211°.

ANALYSIS: Calculated for $C_{11}H_{11}ClN_4O_2S_2$: 39.93%C; 3.35%H; 16.94%N. Found: 39.98%C; 3.31%H; 16.88%N.

EXAMPLE 42

N-(N',N'-Diethylaminomethylene)-3-phenyl-1,2,4-thiadiazole-5-sulfonamide

Thionyl chloride (4.5 ml) was added dropwise to a solution of 3.0 g of 3-phenyl-1,2,4-thiadiazole-5-sulfonamide in 12 ml of 3-phenyl-1,2,4-thiadiazole-5-sulfonamide in 12 ml of dry N,N-diethylformamide at −5°. The resulting mixture was stirred at room temperature for 6 hours, poured into ice water and the precipitated solids were collected, washed with water and taken up in dichloromethane. The organics were washed with water (3 ×) and saturated sodium chloride solution and dried over anhydrous magnesium sulfate. Concentration and drying in vacuo gave an oil which solidified subsequently. Trituration with ether and hexane gave 2.6 g of solid, m.p. 105°–107°.

ANALYSIS: Calculated for $C_{13}H_{16}N_4O_2S_2$: 48.13%C; 4.97%H; 17.27%N. Found: 48.03%C; 4.81%H; 17.22%N.

EXAMPLE 43

N-[1-(N',N'-Dimethylamino)ethylidene]-3-phenyl-1,2,4-thiadiazole-5-sulfonamide

N,N-Dimethylacetamide dimethyl acetal (95%, 3.8 ml) was added dropwise to a suspension of 4.0 g of 3-phenyl-1,2,4-thiadiazole-5-sulfonamide in 30 ml of dry acetonitrile. After stirring at room temperature for one hour, the resulting mixture was diluted with 50 ml of hexane/ether (5:3) and stirred for 30 minutes. The precipitated solids were collected, washed with hexane and dried to give 3.7 g of solid, m.p. 146°–148°.

ANALYSIS: Calculated for $C_{12}H_{14}N_4O_2S_2$: 46.43%C; 4.55%H; 18.05%N. Found: 46.11%C; 4.54%H; 18.11%N.

EXAMPLE 44

N-[1-(N',N'-Dimethylamino)ethylidene]-3-(2-methylphenyl)-1,2,4-thiadiazole-5-sulfonamide To a suspension of 3 g of 3-(2-methylphenyl)-1,2,4-thiadiazole-5-sulfonamide in 22 ml of acetonitrile, 2.8 ml of N,N-dimethylacetamide dimethylacetal (95%) was added dropwise. The mixture was stirred for 1 hour. The resulting suspension was diluted with 50 ml of hexane/ether (5:3) and stirred for 30 minutes. The solid was collected and washed with hexane to give 3.08 g of solid, m.p. 153°–155° C.

ANALYSIS: Calculated for $C_{13}H_{16}N_4O_2S_2$: 48.13%C; 4.97%H; 17.27%N. Found: 48.15%C; 5.23%H; 17.14%N.

EXAMPLE 45

N-(4-Morpholinylmethylene)-3-phenyl-1,2,4-thiadiazole-5-sulfonamide

Thionyl chloride (4.5 ml) was added dropwise to 3.0 g of 3-phenyl-1,2,4-thiadiazole-5-sulfonamide in 15 ml of dry N-formylmorpholine at −5°. The resulting mixture was stirred at room temperature for 3 hours, poured into ice water and stirred for 15 minutes. The solids were collected, washed with water, dried, triturated with ether, washed with hexane and dried (in vacuo, $P_2O_5$). Recrystallization from benzene/hexane gave 1.1 g of solid, m.p. 185°–187°.

ANALYSIS: Calculated for $C_{13}H_{14}N_4O_3S_2$: 46.14%C; 4.17%H; 16.56%N. Found: 46.32%C; 4.15%H; 16.52%N.

EXAMPLE 46

N-(4-Morpholinylmethylene)-3-(2-methylphenyl)-1,2,4-thiadiazole-5-sulfonamide

To a solution of 3.5 g of 3-(2-methylphenyl)-1,2,4-thiadiazole-5-sulfonamide in 18 ml of N-formylmorpholine at −5° C. was added 5 ml of thionyl chloride. The resulting mixture was stirred for 3 hours at room temperature, then poured into ice water and stirred for 30 minutes. The solid was collected, washed with water and sucked dry. The solid was then triturated with ether, ether/hexane (1:1) and hexane successively. The product was dried ($P_2O_5$) to give 4.52 g of solid, m.p. 151°–153° C.

ANALYSIS: Calculated for $C_{14}H_{16}N_4O_3S_2$: 47.71%C; 4.58%H; 15.90%N. Found: 47.42%C; 4.60%H; 15.73%N.

EXAMPLE 47

3-(2-Fluorophenyl)-1,2,4-thiadiazole-5-sulfenamide

A solution of 29.5 g of 5-mercapto-3-(2-fluorophenyl)-1,2,4-thiadiazole in 550 ml of 4.5% NaOH and a solution prepared by diluting 180 ml of 10% NaOCl to 550 ml with water were added dropwise simultaneously to 1450 ml of $NH_4OH$ solution maintained at 0° C. with an ice/methanol bath. The resulting mixture was stirred for 30 minutes and the solids were collected, washed with water and dried under high vacuum ($P_2O_5$) to give 19.0 g of solid, mp 151°–2° dec.

ANALYSIS: Calculated for $C_8H_6FN_3S_2$: 42.27%C; 2.66%H; 18.49%N. Found: 42.15%C; 2.45%H; 18.13%N.

EXAMPLE 48

3-[2-(Trifluoromethyl)phenyl]-1,2,4-thiadiazole-5-sulfenamide

A solution of 15.5 g of 5-mercapto-3-[2-(trifluoromethyl)phenyl-1,2,4-thiadiazole in 207 ml of 5% NaOH and a solution prepared by diluting 130 m of 5.25% NaOCl to 207 ml with water were added dropwise simultaneously to 560 ml of $NH_4OH$ solution maintained at 0° C. with an ice/methanol bath. The resulting mixture was stirred for 30 minutes and the solid were collected, washed with water and dried under high vacuum (with $P_2O_5$) to give 13.5 g of solid, mp 137°–140° dec.

ANALYSIS: Calculated for $C_9H_6F_3N_3S_2$: 38.98%C; 2.18%H; 15.15%N. Found: 38.86%C; 2.17%H; 15.13%N.

EXAMPLE 49

3-(2-Fluorophenyl)-1,2,4-thiadiazole-5-sulfonamide

A solution of 24 g of 85% m-chloroperbenzoic acid in 150 ml of dimethoxyethane was added dropwise to a solution of 12 g of 3-(2-fluorophenyl)-1,2,4-thiadiazole-5-sulfenamide in 600 ml of dimethoxyethane at −5° (ice/methanol bath). The resulting solution was stirred at room temperature for 14 hours. Concentration gave a solid mass which was stirred with 300 ml of saturted $NaHCO_3$ solution for 1.5 hours, filtered, washed with water and air dried. Recrystallization from 3:1 $CH_3OH/H_2O$ (175 ml) gave 9.8 g of crystals, mp 177°–179°.

ANALYSIS: Calculated for $C_8H_6FN_3O_2S_2$: 37.06%C; 2.33%H; 16.21%N. Found: 37.35%C; 2.15%H; 16.16%N.

EXAMPLE 50

3-[2-(Trifluoromethyl)phenyl]-1,2,4-thiadiazole-5-sulfonamide

A solution of 12.7 g of m-chloroperbenzoic acid in 70 ml of dimethoxyethane was added dropwise over 1 hour to a solution of 8 g of 3-[2-(trifluoromethyl)phenyl]-1,2,4-thiadiazole-5-sulfenamide in 190 ml of dimethoxyethane at −5° C. (ice/methanol bath). The resulting solution was stirred at room temperature overnight. Concentration gave a solid mass which was crushed and stirred with 250 ml of $NaHCO_3$ solution for 2 hours, filtered, washed with water and dried to give 6.9 g of crude product. This was recrystallized from methanol/water (3:1) to give 6.2 g of a solid, mp 128°–130°.

ANALYSIS: Calculated for $C_9H_6F_3N_3O_2S_2$: 34.95%C; 1.96%H; 13.59%N. Found: 35.10%C; 1.94%H; 13.23%N.

We claim:

1. A compound having the formula

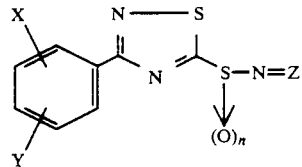

where n is 0, 1 or 2; X and Y are independently hydrogen, loweralkyl, loweralkoxy, arylloweralkyl, aryloxy, halogen, —$CF_3$, —$NO_2$, —OH, —$OCOR_1$,

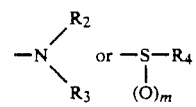

where $R_1$ is loweralkyl, arylloweralkyl, aryl or loweralkoxy, $R_2$ is hydrogen, loweralkyl or loweralkylcarbonyl, $R_3$ is hydrogen or loweralkyl, or the group —$NR_2R_3$ as a whole is

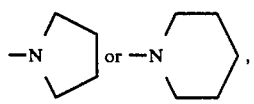

m is 0, 1 or 2, and $R_4$ is hydrogen, loweralkyl or aryl; and Z is ($R_5$, $R_6$)

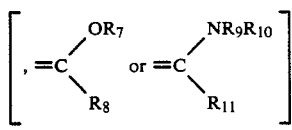

where $R_5$ and $R_6$ are each independently hydrogen or loweralkyl; or a pharmaceutically acceptable salt thereof.

2. A compound as defined in claim 1, where X and Y are each independently hydrogen, loweralkyl, loweralkoxy, halogen, —OH or —OCOR$_1$.

3. A compound as defined in claim 1, where $R_5$ and $R_6$ are hydrogen.

4. A compound as defined in claim 1, where $R_5$ and $R_6$ are hydrogen.

5. A compound as defined in claim 1, where n is 0.
6. A compound as defined in claim 2, where n is 0.
7. A compound as defined in claim 1, where n is 1.
8. A compound as defined in claim 2, where n is 1.
9. A compound as defined in claim 1, where n is 2.
10. A compound as defined in claim 2, where n is 2.
11. A compound as defined in claim 3, where n is 2.
12. A compound as defined in claim 4, where n is 2.
13. The compound as defined in claim 6, which is 3-phenyl-1,2,4-thiadiazole-5-sulfenamide.
14. The compound as defined in claim 6, which is 3-(2-methylphenyl)-1,2,4-thiadiazole-5-sulfenamide.
15. The compound as defined in claim 6, which is 3-(2-methoxyphenyl)-1,2,4-thiadiazole-5-sulfenamide.
16. The compound as defined in claim 6, which is 3-(3-methoxyphenyl)-1,2,4-thiadiazole-5-sulfenamide.
17. The compound as defined in claim 6, which is 3-(4-methoxyphenyl)-1,2,4-thiadiazole-5-sulfenamide.
18. The compound as defined in claim 6, which is 3-(2-chlorophenyl)-1,2,4-thiadiazole-5-sulfenamide.
19. The compound as defined in claim 6, which is 3-(3-chlorophenyl)-1,2,4-thiadiazole-5-sulfenamide.
20. The compound as defined in claim 6, which is 3-(4-chlorophenyl)-1,2,4-thiadiazole-5-sulfenamide.
21. The compound as defined in claim 8, which is 3-(2-methylphenyl)-1,2,4-thiadiaozle-5-sulfinamide.
22. The compound as defined in claim 4, which is 3-(4-methoxyphenyl)-1,2,4-thiadiazole-5-sulfinamide.
23. The compound as defined in claim 8, which is 3-(2-chlorophenyl)-1,2,4-thiadiazole-5-sulfinamide.
24. The compound as defined in claim 12, which is 3-phenyl-1,2,4-thiadiazole-5-sulfonamide.
25. The compound as defined in claim 12, which is 3-(2-methylphenyl)-1,2,4-thiadiazole-5-sulfonamide.
26. The compound as defined in claim 12, which is 3-(2-methoxyphenyl)-1,2,4-thiadiazole-5-sulfonamide.
27. The compound as defined in claim 12, which is 3-(3-methoxyphenyl)-1,2,4-thiadiazole-5-sulfonamide.
28. The compound as defined in claim 12, which is 3-(4-methoxyphenyl)-1,2,4-thiadiazole-5-sulfonamide.
29. The compound as defined in claim 12, which is 3-(2-chlorophenyl)-1,2,4-thiadiazole-5-sulfonamide.
30. The compound as defined in claim 12, which is 3-(3-chlorophenyl)-1,2,4-thiadiazole-5-sulfonamide.
31. The compound as defined in claim 12, which is 3-(4-chlorophenyl)-1,2,4-thiadiazole-5-sulfonamide.
32. The compound as defined in claim 12, which is 3-(3-hydroxyphenyl)-1,2,4-thiadiazole-5-sulfonamide.
33. The compound as defined in claim 12, which is 3-(4-hydroxyphenyl)-1,2,4-thiadiazole-5-sulfonamide.
34. The compound as defined in claim 12, which is 4-(5-sulfamoyl-1,2,4-thiadiazol-3-yl)phenyl 2,2-dimethylpropionate.
35. The compound as defined in claim 6, which is 3-(2-bromophenyl)-1,2,4-thiadiazole-5-sulfenamide.
36. The compound as defined in claim 6, which is 3-(4-bromophenyl)-1,2,4-thiadiazole-5-sulfenamide.
37. The compound as defined in claim 6, which is 3-(2-fluorophenyl)-1,2,4-thiadiazole-5-sulfenamide.
38. The compound as defined in claim 6, which is 3-(4-nitrophenyl)-1,2,4-thiadiazole-5-sulfenamide.
39. The compound as defined in claim 6, which is 3-(2-isopropylphenyl)-1,2,4-thiadiazole-5-sulfenamide.
40. The compound as defined in claim 6, which is 3-(4-isopropylphenyl)-1,2,4-thiadiazole-5-sulfenamide.
41. The compound as defined in claim 6, which is 3-(4-ethoxyphenyl)-1,2,4-thiadiazole-5-sulfenamide.
42. The compound as defined in claim 6, which is 3-[2-(methylthio)phenyl]-1,2,4-thiadiazole-5-sulfenamide.
43. The compound as defined in claim 6, which is 3-[2-(trifluoromethyl)phenyl]-1,2,4-thiadiazole-5-sulfenamide.
44. The compound as defined in claim 6, which is 3-[4-(trifluoromethyl)phenyl]-1,2,4-thiadiazole-5-sulfenamide.
45. The compound as defined in claim 11, which is 3-(2-bromophenyl)-1,2,4-thiadiazole-5-sulfonamide.
46. The compound as defined in claim 11, which is 3-(4-bromophenyl)-1,2,4-thiadiazole-5-sulfonamide.
47. The compound as defined in claim 11, which is 3-(4-ethoxyphenyl)-1,2,4-thiadiazole-5-sulfonamide.
48. The compound as defined in claim 11, which is 3-(2-fluorophenyl)-1,2,4-thiadiazole-5-sulfonamide.
49. The compound as defined in claim 11, which is 3-(4-nitrophenyl)-1,2,4-thiadiazole-5-sulfonamide.
50. The compound as defined in claim 11, which is 3-(4-aminophenyl)-1,2,4-thiadiazole-5-sulfonamide.
51. The compound as defined in claim 11, which is 3-[2-(methylsulfonyl)phenyl]-1,2,4-thiadiazole-5-sulfonamide.
52. The compound as defined in claim 11, which is 3-(2-isopropylphenyl)-1,2,4-thiadiazole-5-sulfonamide.
53. The compound as defined in claim 11, which is 3-(4-isopropylphenyl)-1,2,4-thiadiazole-5-sulfonamide.
54. The compound as defined in claim 11, which is 3-[2-(trifluoromethyl)phenyl]-1,2,4-thiadiazole-5-sulfonamide.
55. The compound as defined in claim 12, which is 3-[4-(trifluoromethyl)phenyl]-1,2,4-thiadiazole-5-sulfonamide.
56. The compound as defined in claim 12, which is 3-[4-(isobutoxycarbonyl)oxyphenyl]-1,2,4-thiadiazole-5-sulfonamide.
57. The compound as defined in claim 12, which is 3-(4-phenoxyphenyl)-1,2,4-thiadiazole-5-sulfonamide.
58. The compound as defined in claim 1, which is N-methyl-3-(4-ethoxyphenyl)-1,2,4-thiadiazole-5-sulfonamide.
59. A pharmaceutical composition comprising an effective glaucoma alleviating amount of a compound as defined in claim 1 and a carrier therefor.
60. A method of treating a patient in need of relief from glaucoma which comprises administering to the patient an effective amount of a compound as defined in claim 1.

* * * * *